United States Patent
Gross et al.

(10) Patent No.: US 8,349,023 B2
(45) Date of Patent: Jan. 8, 2013

(54) AFTER TREATMENT FOR COLOR FIXATION

(75) Inventors: Wibke Gross, Hueckelhoven (DE); Georg Knuebel, Duesseldorf (DE); Astrid Kroos, Monheim (DE); Ralph Nemitz, Juechen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/314,640

(22) Filed: Dec. 8, 2011

(65) Prior Publication Data

US 2012/0080046 A1   Apr. 5, 2012

Related U.S. Application Data

(63) Continuation of application No. PCT/EP2010/055599, filed on Apr. 27, 2010.

(30) Foreign Application Priority Data

Jun. 8, 2009  (DE) .......................... 10 2009 026 817

(51) Int. Cl.
*A61Q 5/10* (2006.01)
*A61Q 5/00* (2006.01)

(52) U.S. Cl. .................. 8/405; 8/406; 8/442; 424/70.1; 424/70.6

(58) Field of Classification Search .............. 8/405, 406, 8/442; 424/70.1, 70.6
See application file for complete search history.

(56) References Cited

U.S. PATENT DOCUMENTS 6,371,993 B1 * 4/2002 Moeller et al. ................... 8/407

FOREIGN PATENT DOCUMENTS

| DE | 102007047685 A1 | 7/2008 |
|---|---|---|
| WO | 2010130510 A2 | 11/2010 |
| WO | 2010130513 A2 | 11/2010 |
| WO | 2010130526 A2 | 11/2010 |
| WO | 2010142493 A2 | 12/2010 |

OTHER PUBLICATIONS

STIC Search Report dated Sep. 19, 2012.*
Schrader, Karlheinz. Grundlagen und Rezepturen der Kosmetika (Fundamentals and Formulations of Cosmetics), 2, Hüthig Buch Verlag GmbH, Heidelberg 1989.

* cited by examiner

*Primary Examiner* — Eisa Elhilo
(74) *Attorney, Agent, or Firm* — David LeCroy

(57) ABSTRACT

Cosmetic hair post-treatment agent for improving washing fastness of coloring processes produced on hair and for color fixing, the post-treatment agent containing, in a cosmetic carrier, at least one acetylpyridinium derivative of formula (I) wherein R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

8 Claims, No Drawings

AFTER TREATMENT FOR COLOR FIXATION

CROSS REFERENCE TO RELATED APPLICATIONS

This application is a continuation of International Patent Application No. PCT/EP2010/055599 filed 27 Apr. 2010, which claims priority to German Patent Application No. 10 2009 026 817.0 filed 8 Jun. 2009, both of which are incorporated herein by reference.

The present invention relates to agents and methods for the post-treatment of hair colored preferably in oxidative fashion, an improvement in washing fastness, particularly in the case of reddish shades being achieved by the post-treatment. The post-treatment agents contain for this purpose a specific cationic acetylpyridinium derivative. The present invention further relates to a multi-component packaging unit (kit) having a coloring agent for hair, in particular, an oxidative coloring agent, preferably for reddish shades, in combination with a developer preparation and post-treatment agent.

Modification of the shape and color of hair represents an important sector of modern cosmetology. The appearance of the hair can thereby be adapted both to current fashion trends and to the individual tastes of the particular person. One skilled in the art knows a variety of coloring systems, depending on the requirements for the coloring process, for providing color-modifying cosmetic agents to keratin-containing fibers such as human hair.

Oxidative coloring agents are used for permanent, intense coloring processes with corresponding fastness properties. Such coloring agents usually contain oxidation dye precursor products, subdivided into developer components and coupler components which, under the influence of oxidizing agents or atmospheric oxygen, form the actual dyes. Oxidative coloring agents are known for providing long-lasting color results. For temporary coloring, typically coloring or toning agents containing substantive dyes are used as a coloring component. These are dye molecules that absorb directly onto the substrate and do not require an oxidative process in order to form the color. Lastly, a great deal of attention has been directed to a further coloring method in which precursors of melanin, a natural hair coloring substance, are applied onto the substrate (e.g., hair) and then form bioanalogous dyes in the hair in the context of oxidative processes. If substrates are to be lightened or bleached, the dyes that color the substrate are decolorized, usually oxidatively using corresponding oxidizing agents such as hydrogen peroxide.

In addition to the production of natural shades (typically used for discreet concealment of gray hair), the formation of "fashion" shades is a principal area of application for oxidative hair colors (oxidative coloring agents). Intense red, red-brown, and copper shades are a particular focus of the "fashion" color palette. One skilled in the art has known for some time, however, that most red shades are weak with respect to washing fastness, which is manifested as an undesired diminution in color intensity after repeated hair washing. If the hair structure is damaged by environmental influences such as perspiration, solar irradiation, or previous cosmetic treatments such as permanent waving or bleaching, color loss resulting from washing-out can occur that much more quickly.

A loss of color intensity is perceived as particularly disadvantageous with bright "fashion" tones. An agent or method that can satisfactorily resolve this disadvantage is not yet known in the literature. The present invention therefore attempts to make available a method by which color fixing after an oxidative color process can be enhanced and washing fastness of existing red shades can be improved. Color loss or color bleeding after repeated hair washing can thereby be decreased. There have been so far only unsatisfactory approaches to improving, in particular, the washing fastness of red shades on damaged hair, and this therefore represents a particular challenge to the developer of new coloring and post-treatment systems.

It was not foreseeable that the washing stability of red shades can be decisively improved by applying a post-treatment agent containing at least one specific cationic acetylpyridinium derivative. The substance class of acetylpyridinium derivatives according to the present invention is already known from the literature as an agent for generating colors on hair (DE 197 45 356) or as agents for lightening hair (DE 10 2007 047685). These Applications provide one skilled in the art, however, with absolutely no instruction as to improvements in the color retention of oxidative color results, particularly red shades.

A first subject of the present invention is therefore directed towards use of a cosmetic post-treatment agent to improve washing fastness of coloring processes produced on hair and for color fixing, wherein the post-treatment agent contains, in a cosmetic carrier, at least one acetylpyridinium derivative of formula (I)

wherein
R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

Post-treatment agents according to the first subject of the invention contain the active substances in a cosmetic carrier. The cosmetic carrier is preferably aqueous, alcoholic, or aqueous alcoholic. Such carriers include creams, emulsions, gels, or also surfactant-containing foaming solutions, for example, shampoos, foam aerosols, or other preparations suitable for utilization on the hair. For purposes of the invention, an "aqueous" carrier contains at least 40 wt %, particularly 50 wt % water. "Aqueous alcoholic" carriers are to be understood for purposes of the present invention as aqueous compositions containing 3 to 70 wt % of a $C_1$ to $C_4$ alcohol, particularly ethanol or isopropanol. Agents according to the present invention can additionally contain organic solvents such as methoxybutanol, ethyl diglycol, 1,2-propylene glycol, n-propanol, n-butanol, n-butylene glycol, glycerol, diethylene glycol monomethyl ether, and diethylene glycol mono-n-butyl ether. All water-soluble organic solvents are preferred in this context. Preferred agents additionally contain a non-aqueous solvent. Particularly preferred agents according to the present invention contain the solvent at a concentration from 0.1 to 30 wt %, preferably at a concentration from 1 to 20 wt %, very particularly preferably at a concentration from 2 to 10 wt %, based on total agent.

Agents used according to the present invention contain as an essential ingredient an acetylpyridinium derivative according to formula (I). Examples of residues recited as substituents of compounds of formula (I) are listed below:

Examples of $C_1$ to $C_6$ alkyl residues are —$CH_3$, —$CH_2CH_3$, —$CH_2CH_2CH_3$, —$CH(CH_3)_2$, $CH_3CH_2CH_2CH_3$, $CH_2CH(CH_3)_2$, $CH(CH_3)CH_2CH_3$, —$C(CH_3)_3$.

Examples of a $C_2$ to $C_6$ alkenyl group are a prop-2-enyl group (allyl group), a 2-methyl-prop-2-enyl group, a but-3-enyl group, a but-2-enyl group, a pent-4-enyl group, or a pent-3-enyl group, the prop-2-enyl group being preferred.

Examples of a $C_2$ to $C_6$ hydroxyalkyl are —$CH_2CH_2OH$, —$CH_2CH_2CH_2OH$, —$CH_2CH(OH)CH_3$, and —$CH_2CH_2CH_2CH_2OH$, the —$CH_2CH_2OH$ group being preferred.

Examples of $C_1$ to $C_6$ alkoxy-$C_2$ to $C_6$ alkyl groups are —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$.

Examples of a carboxy-$C_1$ to $C_6$ alkyl group are the carboxymethyl group, the 2-carboxyethyl group, or the 3-carboxypropyl group.

Examples of aryl-$C_1$ to $C_6$ alkyl groups are the benzyl group and the 2-phenylethyl group.

Examples of a heteroaryl-$C_1$ to $C_6$ alkyl group are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group, or the pyrazol-1-ylethyl group.

Examples of an aryl group are the phenyl group, the 1-naphthyl group, or the 2-naphthyl group.

Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group, or the pyrazol-4-yl group.

In an embodiment of the present invention, those compounds according to formula (I) are preferred wherein R1 of the general structure (I) is a $C_1$ to $C_6$ alkyl group, a $C_2$ to $C_6$ alkenyl group, or a $C_2$ to $C_6$ hydroxyalkyl group.

It is particularly preferred according to the present invention if the residue R1 is a $C_1$ to $C_6$ alkyl group, preferably methyl, ethyl, n-propyl, or isopropyl, and particularly preferably methyl.

It is preferred if the anion $X^-$ according to formula (I) is chosen from halide, particularly chloride, bromide, and iodide, benzenesulfonate, p-toluenesulfonate, $C_1$ to $C_4$ alkylsulfonate, trifluoromethansulfonate, acetate, trifluoroacetate, perchlorate, ½-sulfate, hydrogensulfate, tetrafluorborate, hexafluorphosphate, or tetrachlorozincate. It is particularly favored according to the present invention if the physiologically acceptable anion $X^-$ is a halide ion (particularly chloride or bromide), hydrogensulfate, ½-sulfate, p-toluenesulfonate, benzenesulfonate, or acetate.

It has been found that acetylpyridinium derivatives according to formula (I) possess particularly advantageous properties according to the present invention if they carry the acetyl group in either the 2- or the 4-position on the pyridine ring. A further embodiment of the present invention is therefore that wherein the agent contains, as an acetylpyridinium derivative according to formula (I), at least one 2-acetylpyridinium derivative and/or 4-acetylpyridinium derivative.

Suitable acetylpyridinium derivatives are, in this context, the physiologically acceptable salts that contain as a cation an acetylpyridinium derivative chosen from 4-acetyl-1-methylpyridinium, 4-acetyl-1-allylpyridinium, 4-acetyl-1-(2-hydroxyethyl)pyridinium, 2-acetyl-1-methylpyridinium, 2-acetyl-1-allylpyridinium, and 2-acetyl-1-(2-hydroxyethyl)pyridinium.

Those agents wherein the acetylpyridinium derivative according to formula (I) is chosen from 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium chloride, 4-acetyl-1-methylpyridinium hydrogensulfate, 4-acetyl-1-methylpyridinium acetate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium chloride, 4-acetyl-1-allylpyridinium hydrogensulfate, 4-acetyl-1-allylpyridinium acetate, 2-acetyl-1-methylpyridinium p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogensulfate, 2-acetyl-1-methylpyridinium acetate, 2-acetyl-1-allylpyridinium p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogensulfate, and/or 2-acetyl-1-allylpyridinium acetate, are particularly suitable according to the present invention.

Particularly advantageous post-treatment agents are those wherein the acetylpyridinium derivative according to formula (I) is chosen from 4-acetyl-1-methylpyridinium p-toluenesulfonate and/or 2-acetyl-1-methylpyridinium p-toluenesulfonate, in particular 4-acetyl-1-methylpyridinium p-toluenesulfonate.

In one embodiment, the post-treatment agents used according to the present invention contain the acetylpyridinium derivative of formula (I) at a proportion of 0.05 to 10 wt %, preferably 0.1 to 7.5 wt %, more preferably 0.2 to 6.5 wt %, and particularly 0.5 to 5 wt %, based on total weight of the ready-to-use agent.

Use of post-treatment agents containing acetylpyridinium derivatives of formula (I) is particularly suitable for color fixing of oxidative coloring processes.

An embodiment of this subject of the invention is therefore characterized in that use of the aforesaid post-treatment agent occurs in order to improve washing fastness and for color fixing of oxidative coloring processes.

"Oxidative coloring processes" are, for purposes of the invention, coloring processes for development of which oxidative coloring agents were used. Such coloring agents usually contain as color-modifying components oxidation dye precursor products (developer components and coupler components) that, under the influence of oxidizing agents or atmospheric oxygen, form among one another the actual dyes.

Oxidation dye precursor products are preferably used in a quantity from 0.005 to 25 wt %, preferably from 0.05 to 20 wt %, and particularly preferably from 0.1 to 15 wt %, based on total ready-to-use oxidative coloring agent.

Oxidative coloring agents preferably contain at least one oxidation dye precursor product of the developer type and at least one oxidation dye precursor product of the coupler type.

Developer and coupler components are usually used in free form. In the case of substances having amino groups, however, it may be preferred to use them in salt form, particularly in the form of the hydrochlorides and hydrobromides or the sulfates.

Developer components according to the present invention are chosen from p-phenylenediamines, binuclear developer components, p-aminophenols, o-aminophenols, heterocyclic developer components, and/or the derivatives of the aforesaid substance classes. The developer components are preferably used in an amount from 0.005 to 20 wt %, preferably 0.1 to 15 wt %, based on total ready-to-use oxidative coloring agent.

Preferred p-phenylenediamines include one or more compounds from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl)-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane, as well as physiologically acceptable salts thereof Particularly preferred p-phenylenediamine derivatives according to the present invention include at least one compound from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine, and their physiologically acceptable salts.

It may furthermore be preferred according to the present invention to use as developer components compounds having at least two aromatic nuclei that are substituted with amino and/or hydroxyl groups. Preferred binuclear developer components are chosen from at least one of the following compounds: N,N-bis-(2-hydroxyethyl)-N,N'-bis-(4'-aminophenyl)-1,3-diaminopropan-2-ol, N,N'-bis-(2-hydroxyethyl)-N,N-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-[4-(methylamino)phenyl]tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, as well as physiologically acceptable salts thereof. Particularly preferred binuclear developer components are selected from among N,N-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, or one of the physiologically acceptable salts of these compounds.

It may furthermore be preferred according to the present invention to use as a developer component a p-aminophenol derivative or one of the physiologically acceptable salts thereof. Preferred p-aminophenols include p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-[(2-hydroxyethylamino)methyl]phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof. Particularly preferred compounds are p-aminophenol, 4-amino-3-methylphenol, 4-amino-2-aminomethylphenol, 4-amino-2-(1,2-dihydroxyethyl)phenol, and 4-amino-2-(diethylaminomethyl)phenol, or one of the physiologically acceptable salts of said compounds.

The developer component can also be chosen from o-aminophenol and derivatives thereof such as 2-amino-4-methylphenol, 2-amino-5-methylphenol, or 2-amino-4-chlorophenol.

The developer component can also be chosen from heterocyclic developer components, for example, from pyrimidine derivatives, pyrazole derivatives, pyrazolopyrimidine derivatives, resp. physiologically acceptable salts thereof Preferred pyrimidine derivates are the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Preferred pyrazole derivatives are the compounds that are selected from among 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically acceptable salts thereof.

Preferred pyrazolopyrimidine derivates include the derivatives of pyrazolo[1,5-a]pyrimidine and tautomeric forms thereof, if a tautomeric equilibrium exists. The pyrazolo[1,5a]pyrimidines can be chosen from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]-pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine, as well as physiologically acceptable salts thereof and tautomeric forms thereof, if a tautomeric equilibrium exists.

Very particularly preferred developer components are chosen from at least one of p-phenylenediamine, p-toluylenediamine, 2-(2-hydroxyethyl)-p-phenylenediamine, dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)-propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as physiologically acceptable salts thereof.

Coupler components alone do not produce any significant color in the context of oxidative coloring, but instead always require the presence of developer components. It is therefore preferred according to the present invention that when at least one coupler component is used, at least one developer component is additionally utilized.

Coupler components according to the present invention are preferably chosen from m-aminophenol, m-diaminobenzene, o-diaminobenzene, o-aminophenol, naphthalene derivatives having at least one hydroxy group, di-resp. trihydroxybenzene, pyridine, pyrimidine, monohydroxy-resp. monoaminoindole, monohydroxy-resp. monoaminoindoline, pyrazolone, benzomorpholine, quinoxaline, and/or derivatives of the aforementioned substance classes. The coupler components are preferably used in an amount from 0.005 to 20 wt %, preferably 0.1 to 15 wt %, based on total ready-to-use oxidative coloring agent.

Preferred m-aminophenols and derivatives thereof are chosen from m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts of the compounds recited above.

Preferred m-diaminobenzenes and their derivatives are chosen from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, and physiologically acceptable salts thereof.

Preferred o-diaminobenzene and their derivatives are chosen from 3,4-diaminobenzoic acid and 2,3-diamino-1-methylbenzene, and physiologically acceptable salts thereof.

Preferred di- or trihydroxybenzenes and derivatives thereof are chosen from resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene.

Preferred pyridine derivatives are chosen from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts of the aforesaid compounds.

Preferred naphthalene derivatives having at least one hydroxy group are chosen from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene.

Preferred indole derivatives are chosen from 4-hydroxyindole, 6-hydroxyindole, and 7-hydroxyindole, and the physiologically acceptable salts of the aforesaid compounds.

Preferred indoline derivatives are chosen from 4-hydroxyindoline, 6-hydroxyindoline, and 7-hydroxyindoline, and the physiologically acceptable salts of the aforesaid compounds.

Preferred pyrimidine derivatives are chosen from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and the physiologically acceptable salts of the aforesaid compounds.

Particularly preferred coupler components are chosen from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl}amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or of the physiologically acceptable salts of the aforesaid compounds.

Developer components and coupler components are used in this context generally in approximately molar quantities with respect to one another. Although molar use has proven useful, a certain excess of individual oxidation dye precursor products is not disadvantageous, so that developer components and coupler components can be present at a molar ratio from 3 to 1 to 1 to 3, particularly 2 to 1 to 1 to 2.

Use of post-treatment agents according to the present invention containing, in a cosmetic carrier, at least one acetylpyridinium derivative of formula (I) has proven particularly advantageous when the oxidative coloring process involves a red, reddish, or red-brown shade. Such shades can be produced preferably using specific oxidation dye precursor products. These include, in particular, heterocyclic oxidation dye precursor products of the developer type.

A further embodiment of the first subject of the invention is therefore characterized in that the post-treatment agent used to improve the washing fastness of oxidative coloring processes, the formation of which color is based on use of at least one oxidation dye precursor product of the developer type chosen from 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine, as well as 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl) amino-1,3-dimethylpyrazole, and physiologically acceptable salts thereof.

Particularly preferably the oxidative coloring has been produced using at least one oxidation dye precursor product of the developer type chosen from 4,5-diamino-1-(2-hydroxyethyl)pyrazole and/or 2,4,5,6-tetraaminopyrimidine.

Red, reddish, or red-brown shades can preferably be generated using special combinations of specific oxidation dye precursor products of the developer type and coupler type. Those post-treatment agents containing, in a cosmetic carrier, at least one acetylpyridinium derivative of formula (I) are used in preferred fashion to improve washing fastness and color fixing of oxidative color processes when at least one developer/coupler combination chosen from—
2,4,5,6-tetraaminopyrimidine and resorcinol;
2,4,5,6-tetraaminopyrimidine and 2-methylresorcinol;
2,4,5,6-tetraaminopyrimidine and 4-chlororesorcinol;
2,4,5,6-tetraaminopyrimidine and 2,6-bis(2'-hydroxyethylamino)-1-methylbenzene;
4,5-diamino-1-(2-hydroxyethyl)pyrazole and resorcinol;
4,5-diamino-1-(2-hydroxyethyl)pyrazole and 2-methylresorcinol;
4,5-diamino-1-(2-hydroxyethyl)pyrazole and 4-chlororesorcinol;
4,5-diamino-1-(2-hydroxyethyl)pyrazole and 3-aminophenol;
4,5-diamino-1-(2-hydroxyethyl)pyrazole and 3-amino-2-chloro-6-methylphenol;
4,5-diamino-1-(2-hydroxyethyl)pyrazole and 5-amino-2-methylphenol;
4,5-diamino-1-(2-hydroxyethyl)pyrazole and 1-hydroxynaphthalene; and
4,5-diamino-1-(2-hydroxyethyl)pyrazole and 2,4-dichloro-m-aminophenol
is used to constitute the color.

For oxidative coloring processes, development of the color from the oxidation dye precursor products can be effected in principle using atmospheric oxygen. It is preferred, however, to utilize a chemical oxidizing agent, particularly when a lightening effect on human hair is desired in addition to color. This lightening effect can be desired regardless of the coloring method. Suitable oxidizing agents are persulfates, peroxodisulfates, chlorites, hypochlorites, and particularly hydrogen peroxide and/or one of the solid addition products thereof with organic or inorganic compounds.

In order to prevent a premature, undesired reaction of the oxidation dye precursor products as a result of the oxidizing agent, the oxidation dye precursor products and the oxidizing agent itself are usefully packaged separately from one another, and brought into contact only immediately before use.

The oxidizing agent preparation preferably contains, as an oxidizing agent, hydrogen peroxide and/or one of the solid addition products thereof with organic or inorganic compounds such as urea, melamine, and sodium borate.

The amount of oxidizing agent in the ready-to-use agent is preferably 0.5 to 12 wt %, more preferably 2 to 10 wt %, and particularly 3 to 6 wt % (calculated as 100% $H_2O_2$), based on total ready-to-use agent.

Oxidizing agent preparations of this kind are preferably aqueous, flowable oxidizing agent preparations. Preferred preparations are those wherein the flowable oxidizing agent preparation contains, based on its weight, 40 to 90 wt %, preferably 50 to 85 wt %, more preferably 55 to 8 wt %, even more preferably 60 to 77.5 wt %, and particularly 65 to 75 wt % water.

The oxidative coloring agent can, however, also be applied onto the hair together with a catalyst that activates oxidation of the dye precursor products (e.g., by atmospheric oxygen). Such catalysts include certain enzymes, iodides, quinones, or metal ions.

It has also proven advantageous if the oxidizing agent preparations contain at least one stabilizer or complexing agent. Particularly preferred stabilizers are phenacetin, alkali benzoates (sodium benzoate) and salicylic acid. All complexing agents of the existing art can also be used. These can belong to various chemical groups, and are preferably used individually or in a mixture with one another. Preferred complexing agents are nitrogen-containing polycarboxylic acids, in particular EDTA, and phosphonates, by preference hydroxyalkane- or aminoalkanephosphonates and in particular 1-hydroxyethane-1,1-diphosphonate (HEDP) resp. the di- or tetrasodium salt thereof, and/or ethylenediaminetetramethylenephosphonate (EDTMP) resp. the hexasodium salt thereof, and/or diethylenetriaminepentamethylenephosphonate (DTPMP) or the hepta- or octasodium salt thereof.

The ready-to-use coloring preparation and the post-treatment agent can contain further adjuvants and additives. For example, it has proven to be advantageous if the coloring preparation, the oxidizing agent preparation, and/or the post-treatment agent contain at least one thickening agent. No limitations exist in principle with regard to this thickening agent. Both organic and entirely inorganic thickening agents can be utilized.

Suitable thickening agents include
anionic synthetic polymers;
cationic synthetic polymers;
naturally occurring thickening agents such as nonionic guar gums, scleroglucan gums or xanthan gums, gum arabic, ghatti gum, karaya gum, tragacanth gum, carrageenan gum, agar-agar, locust bean flour, pectins, alginates, starch fractions and derivatives such as amylose, amylopectin, and dextrins, as well as cellulose derivatives, for example, methyl cellulose, carboxyalkyl celluloses, and hydroxyalkyl celluloses;
nonionic fully synthetic polymers, such as polyvinyl alcohols or polyvinylpyrrolidinone; and inorganic thickening agents, particularly sheet silicates such as bentonite, particularly smectites such as montmorillonite or hectorite.

To further increase the performance of the coloring agent preparation, at least one $SiO_2$ compound such as silicic acid or silicates, in particular water glasses, can additionally be added to the composition according to the present invention. It may be preferred according to the present invention to use the $SiO_2$ compounds in amounts from 0.05 wt % to 15 wt %, preferably from 0.15 wt % to 10 wt %, and very preferably from 0.2 wt % to 5 wt %, based on the anhydrous composition according to the present invention. The quantitative indications reproduce in each case the concentration of $SiO_2$ compounds (without their water component) in the agents.

Use of the aforesaid post-treatment agent further serves to improve the washing fastness, and for color fixing, of coloring processes that derive from substantive dyes. The oxidative coloring agents can also additionally contain at least one substantive dye. These are dyes that absorb directly onto the hair and do not require an oxidative process in order to form the color. Substantive dyes are usually nitrophenylenediamines, nitroaminophenols, azo dyes, anthraquinones, or indophenols. Substantive dyes are known as anionic, cationic, and nonionic substantive dyes. The substantive dyes are preferably used in an amount from 0.001 to 20 wt %, based on the entire application preparation.

Preferred anionic substantive dyes are compounds known under the international designations or commercial names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes such as Basic Blue 7, Basic Blue 26, Basic Violet 2, and Basic Violet 14, aromatic systems that are substituted with a quaternary nitrogen group, for example Basic Yellow 57, Basic Red 76, Basic Blue 99, Basic Brown 16, and Basic Brown 17, as well as substantive dyes having a heterocycle that comprises at least one quaternary nitrogen atom, in particular Basic Yellow 87, Basic Orange 31, and Basic Red 51. The cationic substantive dyes that are marketed under the Arianor trademark are likewise preferred cationic substantive dyes according to the present invention.

Nonionic nitro and quinone dyes and neutral azo dyes are particularly suitable as nonionic substantive dyes. Preferred nonionic substantive dyes are the compounds known under the international designations resp. commercial names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyDamino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Use of post-treatment agents containing acetylpyridinium derivatives of formula (I) is likewise suitable for the color fixing of colors that have been generated using coloring agents having, as color-imparting compounds, at least one bioanalogous dye precursor product and/or at least one oxo dye precursor product.

Bioanalogous dyes used as dye precursors are preferably those indoles and indolines having at least two groups chosen from hydroxy and/or amino groups, preferably as a substituent on the six-membered ring. These groups can carry further substituents, for example, in the form of an etherification or esterification of the hydroxy group or an alkylation of the amino group. In a further embodiment, the coloring agents contain at least one indole derivative and/or indoline derivative. Compositions according to the present invention having precursors of bioanalogous dyes are preferably used as air-oxidizing coloring agents. In this embodiment, the aforesaid compositions consequently do not have an additional oxidizing agent added to them. The dye precursors of bioanalogous dyes are preferably used in an amount from 0.001 to 5 wt %, based on the entire application preparation. The total quantity of substantive dyes is preferably at most 3 wt %.

Preferred derivatives of indoline include 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, as well as 5,6-dihydroxyindoline-2-carboxylic acid, and particularly preferably 5,6-dihydroxyindoline. Preferred derivatives of indole include 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, and in particular 5,6-dihydroxyindole.

A further possibility for imparting color is offered by the use of coloring agents containing oxo dye precursor products. In a further embodiment, oxo dye precursor products can therefore also be used as color-modifying components according to the present invention. Oxo dye precursor products are used preferably as a combination of at least one (oxo1) compound that contains at least one reactive carbonyl group, with at least one (oxo2) compound chosen from C,H-acid compounds and/or compounds having a primary or secondary amino group or hydroxy group.

The aforesaid (oxo1) and (oxo2) components are generally not themselves dyes and are therefore, if considered individually, not suitable by themselves for the coloring of keratin-containing fibers. In combination, they form the actual dyes in the non-oxidizing process of oxo dyeing. The resulting colors possess in some cases color fastness values on the keratin-containing fibers that are comparable with those of oxidative dyeing.

It is nevertheless preferred according to the present invention if (oxo2) are chosen only from among C,H-acid compounds. The (oxo1) and (oxo2) compounds recited above are respectively used, when they are utilized, preferably in an amount from 0.001 to 10 wt %, particularly 0.01 to 5 wt %, based on total weight of the ready-to-use agent.

It is not necessary for the oxidation dye precursor products, substantive dyes, oxo dye precursor products, or bioanalogous dyes to represent uniform compounds in each case. It is instead possible, as a function of the manufacturing method for the individual dyes, for further components to be also contained in subordinate quantities, provided they do not disadvantageously influence the coloring result or do not need to be excluded for other (e.g., toxicological) reasons.

Use according to the present invention of the post-treatment agent for color fixing occurs subsequently to the (preferably oxidative) coloring of the hair.

A further subject of the present invention is therefore a method for coloring and post-treating human hair, comprising:
a) subjecting the hair to a coloring process using a color-imparting agent,
b) washing out of the hair the color-carrying substance and optionally drying the hair, and
c) subjecting the hair to post-treatment with a cosmetic hair treatment agent containing, in a cosmetic carrier, at least one acetylpyridinium derivative of formula (I),

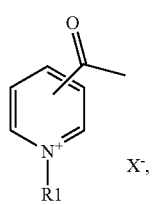

wherein
R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and
$X^-$ is a physiologically acceptable anion.

In a particular embodiment of this method, in a first step a), the hair is subjected to an oxidative coloring process using an oxidative coloring agent. The first step a) is then characterized by an oxidative coloring of human hair. For this, a ready-to-use coloring preparation containing, in a cosmetic carrier, at least one oxidation dye precursor product and optionally an oxidizing agent is applied as an oxidative coloring agent onto the hair and left on the hair for a contact time from 5 to 45 minutes.

The oxidative coloring agent can be produced immediately before utilization by mixing a preparation containing, in a cosmetic carrier, at least one oxidation dye precursor product with an oxidizing agent preparation.

Contact time of the ready-to-use color preparation is preferably 5 to 45 min, more preferably 10 to 40 min, and particularly 15 to 35 min.

During the contact time of the agent on the fibers, it may be advantageous to assist the coloring operation by delivering heat. Heat delivery can occur by an external heat source, such as warm air from a warm air blower, and also, in particular in a hair coloring process on living subjects, by way of the body temperature of the subject. With the latter option, the portion to be colored is usually covered with a hood. A contact phase at room temperature is likewise in accordance with the present invention. The temperature during the contact time is in particular from 20° C. to 40° C., more particularly from 25° C. to 38° C. The oxidative coloring agents already produce intense coloring at physiologically acceptable temperatures of 45° C. or less.

After the contact time has ended, in a second step b) the remaining color-carrying substance is rinsed out of the hair with water or a cleaning agent. A commercial shampoo can serve as a cleaning agent in this context, in which case the cleaning agent can then be omitted and the rinsing-out operation can occur using tap water if the coloring agent possesses a carrier with high surfactant content.

The hair can optionally be dried before the third method step. Post-treatment can, however, also occur on moist hair.

In the method according to the present invention, not too much time elapses between the end of the second method step and the post-treatment of the third method step. Post-treatment follows usually less that 60 min, preferably less than 30 min, in particular less than 10 min, and particularly preferably immediately after the second method step.

In the third method step c), the post-treatment agent according to the present invention is applied onto the (still wet or now dry) hair and left there for 5 to 45 min, preferably 5 to 30 min. During the contact time of the post-treatment agent on the fibers, it may likewise be advantageous to assist the treatment operation by delivering heat. The temperature during the contact time is in particular from 20 to 40° C., more particularly from 25° C. to 38° C.

If the post-treatment agent is used as a "leave-on" product, no further rinsing operation occurs after the post-treatment. In a further embodiment, however, the post-treatment agent can also be used as a "rinse-off" product. In this case a further washing-out operation follows as an additional method step. Statements regarding the second method b) apply here analogously.

The (preferably oxidative) coloring agents and post-treatment agents of the aforesaid subjects of the invention can contain additional active substances, adjuvants, and additives.

The agents are preferably made available as a flowable preparation, and an emulsifier or surfactant is therefore additionally added to them. Surface-active substances are referred to as "surfactants" or "emulsifiers" depending on the application sector, and are chosen from anionic, cationic, zwitterionic, amphoteric, and nonionic surfactants and emulsifiers.

Preferred agents additionally contain at least one anionic surfactant. Preferred anionic surfactants are fatty acids, alkyl sulfates, alkyl ether sulfates, and ethercarboxylic acids having 10 to 20 carbon atoms in the alkyl group and up to 16 glycol ether groups in the molecule. The anionic surfactants are used in amounts from 0.1 to 45 wt %, preferably 1 to 30 wt %, and very particularly from 1 to 15 wt %, based on total amount of the ready-to-use agent.

Preferred agents additionally contain at least one zwitterionic surfactant. Particularly suitable zwitterionic surfactants are betaines and N-alkyl-N,N-dimethylammonium glycinates, N-acylaminopropyl-N,N-dimethylammonium glycinates, and 2-alkyl-3-carboxymethyl-3-hydroxyethylimidazolines. A preferred zwitterionic surfactant is the fatty acid amide derivative known by the INCI name Cocamidopropyl Betaine.

Preferred agents according to the present invention additionally contain at least one amphoteric surfactant. Examples of suitable amphoteric surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred ampholytic surfactants are N-cocalkylaminopropionate, cocacylaminoethylaminopropionate, and $C_{12}$ to $C_{18}$ acyl sarcosine.

It has also proven to be advantageous if the agents further contain nonionogenic surface-active substances. Alkyl polyglycosides have proven successful as preferred nonionic surfactants, as well as alkylene oxide addition products with saturated linear fatty alcohols and fatty acids having 2 to 30 mol ethylene oxide per mol fatty alcohol or fatty acid. Preparations having outstanding properties are likewise obtained when they contain fatty acid esters of ethyoxylated glycerol as nonionic surfactants.

Nonionic, zwitterionic, or amphoteric surfactants are used in amounts of from 0.1 to 45 wt %, preferably 1 to 30 wt %, and particularly 1 to 15 wt %, based on total ready-to-use agent.

Suitable agents according to the present invention can also contain cationic surfactants of the quaternary ammonium compound, esterquat, and amidoamine types. Preferred quaternary ammonium compounds are ammonium halides, as well as imidazolium compounds known by the INCI names Quaternium-27 and Quaternium-83. Further cationic surfactants usable according to the present invention are represented by the quaternized protein hydrolysates. A compound from among the amidoamines that is particularly suitable according to the present invention is represented by the stearamidopropyldimethylamine commercially available under the designation Tegoamid® S 18. Preferred esterquats are quaternized ester salts of fatty acids with triethanolamine, quaternized ester salts of fatty acids with diethanol alkylamines, and quaternized ester salts of fatty acids with 1,2-dihydroxypropyldialkylamines. Such products are marketed, for example, under the trademarks Stepantex®, Dehyquart® and Armocare®. The cationic surfactants are present in the agents preferably in amounts from 0.05 to 10 wt %, based on the entire agent. Quantities from 0.1 to 5 wt % are particularly preferred.

Agents according to the present invention can additionally contain further active substances, adjuvants, and additives such as nonionic polymers, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or non-crosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone polyols), linear polysiloxane(A)-polyoxyalkylene(B) block copolymers, grafted silicone polymers; cationic polymers such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidinone copolymers quaternized with diethyl sulfate, vinylpyrrolidinone/imidazolinium methochloride copolymers, and quaternized polyvinyl alcohol; zwitterionic and amphoteric polymers; anionic polymers such as polyacrylic acids or crosslinked polyacrylic acids; structuring agents such as glucose, maleic acid, and lactic acid, hair-conditioning compounds such as phospholipids, for example lecithin and kephalins; perfume oils, dimethylisosorbide, and cyclodextrins; fiber-structure-improving active substances, in particular mono-, di- and oligosaccharides such as glucose, galactose, fructose, fruit sugars, and lactose; dyes for coloring the agent; anti-dandruff active substances such as piroctone olamine, zinc omadine and climbazol; amino acids and oligopeptides, in particular arginine and/or serine; animal- and/or plant-based protein hydrolysates such as protein hydrolysates of elastin, collagen, keratin, silk, and milk, or protein hydrolysates of almond, rice, bean, potato, and wheat, as well as derivatives in the form of fatty acid condensation products thereof or optionally anionically or cationically modified derivatives; vegetable oils such as macadamia nut oil, palm oil, amaranth seed oil, peach kernel oil, avocado oil, olive oil, coconut oil, rapeseed oil, sesame oil, jojoba oil, soy oil, peanut oil, evening primrose oil, and tea tree oil; light-protection agents such as derivatized benzophenones, cinnamic acid derivatives, and triazines; active substances such as panthenol, pantothenic acid, pantolactone, allantoin, pyrrolidinonecarboxylic acids, and salts thereof, as well as bisabolol; polyphenols, in particular hydroxycinnamic acids, 6,7-dihydroxycumarins, hydroxybenzoic acids, catechins, tannins, leucoanthocyanidine, anthocyanidines, flavanones, flavones, and flavonols; ceramides or pseudoceramides; vitamins, provitamins, and vitamin precursors, in particular of the groups A, $B_3$, $B_5$, $B_6$, C, E, F, and H; plant extracts such as the extracts of aloe vera, angelica, anise, apricot, benzoin, bergamot, birch, nettle, calamus, blackcurrant, costus, hibiscus, oak bark, elemi, tarragon, pine needles, galbanum, geranium, ginseng, grapefruit, guaiac wood, green tea, hamamelis, restharrow, hops, coltsfoot, ginger root, iris, jasmine, chamomile, cardamom, clover, burdock root, pine, kiwi fruit, coconut, coriander, caraway, mountain pine, lavender, lemon grass, lily, lime, linden blossom, lychee, mace, malva, almond, mango, lemon balm, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, spruce, thyme, juniper, vine leaves, hawthorn, wheat, lady's-smock, ylang-ylang, cedar, and lemon; fats and waxes such as fatty alcohols, beeswax, Montan wax, and paraffins; swelling and penetration substances such as glycerol, propylene glycol monoethyl ether, carbonates, hydrogencarbonates, guanidines, ureas, and primary, secondary, and tertiary phosphates; opacifiers such as latex, styrene/PVP and styrene/acrylamide copolymers; luster agents such as ethylene glycol mono- and distearate as well as PEG-3 distearate; pigments, and propellants such as propane/butane mixtures, $N_2O$, dimethyl ether, $CO_2$, and air.

One skilled in the art selects these further substances according to the desired properties of the agents. Regarding further optional components, as well as the quantities of those components used, reference is made to the relevant manuals known to one skilled in the art, for example, Kh. Schrader, Grundlagen and Rezepturen der Kosmetika [Cosmetics fundamentals and formulations], 2nd Ed., Hiithig Buch Verlag, Heidelberg (1989). Additional active substances and adjuvants are used in agents according to the present invention preferably in amounts from 0.0001 to 10 wt %, in particular from 0.0005 to 5 wt %, based on total weight of the application mixture.

A preferred embodiment according to the present invention is one wherein the ready-to-use oxidative coloring agent of the first method step a) has a pH of from 6 to 12, preferably 7 to 11.5, and particularly 8 to 11.

According to a further preferred embodiment according to the present invention, the post-treatment agent containing at least one acetylpyridinium derivative of formula (I) of the third method step c) has a pH of from 2.0 to 8.0, preferably 2.5 to 7.5, and particularly 3.0 to 7.0. The pH values for purposes of the present invention are pH values measured at a temperature of 22° C.

The pH is usually adjusted using pH adjusting agents. One skilled in the art is familiar, for purposes of adjusting the pH, with acidifying and alkalizing agents common in cosmetics. Alkalizing agents used for adjusting the pH are typically chosen from inorganic salts, in particular of the alkali and alkaline-earth metals, organic alkalizing agents, in particular amines, basic amino acids and alkanolamines, and ammonia. Acidifying agents preferred according to the present invention are edible acids such as citric acid, acetic acid, malic acid, or tartaric acid, as well as dilute mineral acids.

Organic alkalizing agents useful according to the present invention are preferably chosen from 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methyl-propan-2-ol, 3-aminopropane-1,2-diol, 2-amino-2-methylpropane-1,3-diol, 2-amino-2-ethyl-1,3-propanediol, N,N-dimethylethanolamine, methylglucamine, triethanolamine, diethanolamine, and tri-isopropanolamine. Alkanolamines preferred according to the present invention are monoethanolamine and triethanolamine. Inorganic alkalizing agents according to the present invention are preferably chosen from sodium hydroxide, potassium hydroxide, calcium hydroxide, barium hydroxide, sodium phosphate, potassium phosphate, sodium silicate, potassium silicate, sodium carbonate, and potassium carbonate. Sodium hydroxide and/or potassium hydroxide are very particularly preferred. Basic amino acids used as alkalizing agents according to the present invention are preferably chosen from L-arginine, D-arginine, D/L-arginine, L-lysine, D-lysine, D/L-lysine, particularly preferably L-arginine, D-arginine, D/L-arginine used as an alkalizing agent for purposes of the invention. Lastly, a further preferred alkalizing agent is ammonia.

Embodiments of the first subject of the invention are valid, mutatis mutandis, for the method of the second subject of the invention.

Use of post-treatment agents according to the present invention for improving, if applicable, the color retention of oxidative coloring processes preferably takes place shortly after the coloring operation. It is therefore useful, for reasons of easier utilization and packaging economy, to make both agents available together to the user.

A further subject of the present invention is therefore a multi-component packaging unit (kit of parts) having at least two components packaged separately from one another, wherein
  i) the first component is a coloring preparation (A) containing, in a cosmetic carrier, at least one color-imparting agent, and
  ii) the second component is a post-treatment agent (C) that contains, in a cosmetic carrier, at least one acetylpyridinium derivative of formula (I),

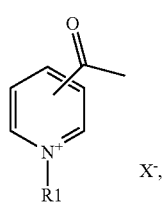

wherein
  R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and
  $X^-$ is a physiologically acceptable anion.

Coloring preparation (A) preferably contains at least one oxidation dye precursor product and/or at least one substantive dye as a color-imparting agent. Coloring preparation (A) is particularly preferably an oxidative coloring agent.

Another embodiment of this subject of the invention is therefore a multi-component packaging unit (kit of parts) having at least three components packaged separately from one another, wherein
  i) the first component is a coloring preparation (A) containing, in a cosmetic carrier, at least one oxidation dye precursor product,
  ii) the second component is an oxidizing agent preparation (B) containing, in a cosmetic carrier, at least one oxidizing agent, and
  iii) the third component is a post-treatment agent (C) containing, in a cosmetic carrier, at least one acetylpyridinium derivative of formula (I),

wherein
  R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and
  $X^-$ is a physiologically acceptable anion.

The components of the multi-package unit are packaged separately from one another in physically different containers.

The term "container" represents, in this context, a receiving capability, regardless of its shape, material, or closure, which embodies the capability of containing substances or substance mixtures. The term "container" therefore includes, without being limited thereto, the interior of a tube, of a pouch or sack, of a canister, of a tin, of a pan, of a bottle, of a glass or a packet, of a carton, of a box, of an envelope, or of another receptacle. The containers can be equipped with a reclosable opening such as a screw closure. This may be advantageous in particular when multiple agents are to be intimately mixed with one another, for example, by shaking before use.

The components of the oxidative coloring preparation can be contained in a double-chamber container having a separate or shared opening. It is preferred, however, to distribute them into different containers and to instruct the consumer to mix them with one another before use.

The multi-component packaging unit (kit of parts) preferably also contains a set of instructions for use. The instructions for use contain, in particular, information, explanations and, if applicable, illustrations for the user (male/female) for using the agents from the containers of the packaging unit in a method in accordance with the second subject of the invention. It may furthermore be preferred if a mixing aid, for example, a dish, an application aid, for example, a comb or brush, and/or personal protection equipment, for example, disposable gloves, are included with the kit.

The embodiments of the preceding subjects of the invention are valid, mutatis mutandis, with regard to preferred embodiments of the multi-component packaging unit according to the present invention.

The following Examples explain the invention without, however, limiting it thereto.

EXAMPLES

1. Manufacturing the Color Cream
The following color cream was manufactured:

| | |
|---|---|
| Hydrenol D [1] | 8.5 g |
| Lorol, technical [2] | 2.0 g |
| Texapon NSO-UP [3] | 20.0 g |
| Dehyton K [4] | 12.5 g |
| Eumulgin B2 [5] | 0.75 g |
| Sodium sulfite | 1.0 g |
| Ammonium sulfate | 1.0 g |
| 4,5-diamino-1-(2-hydroxyethyl)pyrazole, sulfate | 3 mmol |
| Resorcinol | 3 mmol |
| Propylene glycol | 5.0 g |
| Water | to 100 |

The following commercial products were used:
[1] INCI name: Cetearyl Alcohol (Cognis)
[2] INCI name: Coconut Alcohol (Cognis)
[3] INCI name: Sodium Laureth Sulfate; approx. 27.5% active substance (Cognis)
[4] INCI name: Cocamidopropyl Betaine (Cognis)
[5] INCI name: Ceteareth-20 (Cognis)

Hydrenol D and Lorol were melted together with Texapon NSO, Dehyton K, and Eumulgin B2 at 80° C. The melt was then emulsified with the sodium sulfite and ammonium sulfate dissolved in a portion of the water. Oxidation dye precursor products were dissolved while heating in propylene glycol and in a further portion of the water, and added while stirring. The formulation was then topped off up to 100% with water and stirred while cold.

2. Mixing with the Developer Dispersion, and Application

The coloring cream obtained was mixed at a 2:1 ratio with an oxidizing agent preparation having a hydrogen peroxide content of 3 wt %. Damaged strands (bleached twice and permanent-waved twice; Kerling Euro-Natur hair, white) were used for the coloring process. Four times the amount of the ready-to-use mixture was applied onto each strand and left there for 30 minutes at 32° C.

3. Washing-Out Operation

The strands were then rinsed out with lukewarm water, washed with a commercially usual shampoo, and dried.

4. Post-Treatment

For the post-treatment step, a colored strand was treated for 15 minutes at room temperature with the following solution:

| | |
|---|---|
| 4-acetyl-1-methylpyridinium p-toluenesulfonate | 1.00 g |
| Water | to 100 g |
| (pH of the solution = 3.4) | |

A reference strand was treated analogously with water that had been brought to a pH of 3.4 by adding citric acid.

5. Washing-Out Operation

The strands were then rinsed out again with lukewarm water and dried.

6. Colorimetric Measurement

The calibrated strands were measured colorimetrically using a Datacolor Spectraflash 450 colorimeter.

The L*a*b* color space is described by a three-dimensional coordinate system. The L* axis, with endpoints at black (L=0) and white (L=100), reproduces the brightness of a color. The a* axis describes the red or green component of a color. A color having a high proportion of green has a negative 'a' value, and a color having a high proportion of red has a positive 'a' value. The b* axis describes the blue or yellow component of a color. Negative 'b' values represent a color with a high proportion of blue, and positive 'b' values a color having a high proportion of yellow.

The color intensity (chroma) is calculated therefrom using the formula $$C=\sqrt{[(a^*)^2+(b^*)^2]}$$

7. Hair Washing

To simulate the washing-out operation, the hair strands were introduced for 15 minutes into an ultrasonic bath of the Elma company (model T 790/H, level 5) that had been filled with a 1-wt % aqueous Texapon-NSO solution. After drying, another colorimetric measurement was made.

8. Results

TABLE 1

| Comparison treatment | | | | | | |
|---|---|---|---|---|---|---|
| | after 0 hair washes | | | after 6 hair washes | | |
| | a* | b* | $C_0$ | a* | b* | $C_6$ |
| Post-treatment with water | 13.55 | 4.33 | 14.23 | 11.12 | 2.73 | 11.19 |

TABLE 2

| Post-treatment according to the present invention | | | | | | |
|---|---|---|---|---|---|---|
| | after 0 hair washes | | | after 6 hair washes | | |
| | a* | b* | $C_0$ | a* | b* | $C_6$ |
| Post-treatment with 4-acetyl-1-methylpyridinium p-toluenesulfonate solution | 15.31 | 4.43 | 15.94 | 14.60 | 3.62 | 15.04 |

The higher the a* value, the greater the corresponding red proportion of a shade. Immediately after post-treatment with the post-treatment agent according to the present invention, it was already possible to both visually observe and instrumentally sense a greater preservation of the red coloring compared to the reference strand (Δa* value=1.76). This effect was further intensified after six hair washes (Δa* value=3.48), from which it may be concluded that the red constituents of the shade were considerably better fixed due to post-treatment according to the present invention.

It is further evident from the results of Tables 1 and 2 that the chroma loss ($\Delta C=C_0-C_6$) due to repeated hair washing is very much greater for the comparison post-treatment than with the post-treatment agent according to the present invention (ΔC=3.03 not according to the present invention, compared to ΔC=0.90 according to the present invention).

We claim:

1. Cosmetic post-treatment agent for improving the washing fastness of coloring processes produced on hair and for color fixing, comprising, in a cosmetic carrier:
at least one acetylpyridinium derivative of formula (I),

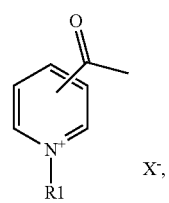

(I)

wherein
R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

2. Agent according to claim 1, wherein the acetylpyridinium derivative is 4-acetyl-1-methylpyridinium p-toluenesulfonate and/or 2-acetyl-1-methylpyridinium p-toluenesulfonate.

3. Agent according to claim 1, wherein the agent improves the washing fastness and color fixing of oxidative coloring processes.

4. Agent according to claim 1, wherein the coloring processes comprises at least one oxidation dye precursor product of the developer type chosen from 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine, as well as 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically acceptable salts thereof.

5. Method for coloring and post-treating human hair, comprising: wherein the hair subjecting hair to a coloring process using a color-imparting agent, washing the color-carrying substance out of the hair and optionally drying the hair, and subjecting the hair to a post-treatment with a cosmetic hair treatment agent comprising, in a cosmetic carrier, at least one acetylpyridinium derivative of formula (I),

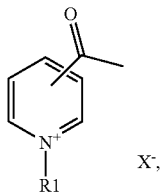

(I)

wherein

R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

6. Method according to claim 5, wherein the hair is subjected to an oxidative coloring process using an oxidative coloring agent.

7. Multi-component packaging unit comprising at least two components packaged separately from one another, wherein i) the first component is a coloring preparation (A) comprising, in a cosmetic carrier, at least one color-imparting agent, and ii) the second component is a post-treatment agent (C) comprising, in a cosmetic carrier, at least one acetylpyridinium derivative of formula (I),

(I)

wherein

R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

8. Multi-component packaging unit (kit of parts) comprising at least three components packaged separately from one another, wherein i) the first component is a coloring preparation (A) comprising, in a cosmetic carrier, at least one oxidation dye precursor product, ii) the second component is an oxidizing agent preparation (B) comprising, in a cosmetic carrier, at least one oxidizing agent, and iii) the third component is a post-treatment agent (C) comprising, in a cosmetic carrier, at least one acetylpyridinium derivative of formula (I),

(I)

wherein

R1 is a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy-$C_2$ to $C_6$ alkyl group, an aryl-$C_1$ to $C_6$ alkyl group, a heteroaryl-$C_1$ to $C_6$ alkyl group, an aryl group, or a heteroaryl group, and $X^-$ is a physiologically acceptable anion.

* * * * *